US006960455B2

(12) United States Patent
Livshits et al.

(10) Patent No.: US 6,960,455 B2
(45) Date of Patent: Nov. 1, 2005

(54) **METHODS OF MAKING AMINO ACIDS USING *E. COLI* TRANSFORMED WITH CSC GENES**

(75) Inventors: Vitaliy Arkadyevich Livshits, Moscow (RU); Vera Georgievna Doroshenko, Moscow (RU); Sergei Vlsdimirovich Mashko, Moscow (RU); Valery Zavenovich Akhverdian, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/841,609

(22) Filed: Apr. 25, 2001

(65) Prior Publication Data

US 2001/0049126 A1 Dec. 6, 2001

(30) Foreign Application Priority Data

Apr. 26, 2000 (RU) ........................................ 2000110350

(51) Int. Cl.$^7$ ................................................ C12P 13/04
(52) U.S. Cl. ........................ 435/106; 435/108; 435/115; 435/116
(58) Field of Search ............................ 435/252.33, 106, 435/115, 116, 108, 252.1

(56) References Cited

U.S. PATENT DOCUMENTS

| 4,346,170 | A | 8/1982 | Sano et al. |
| 5,175,107 | A | 12/1992 | Debabov et al. |
| 5,534,421 | A | 7/1996 | Livshits et al. |
| 5,538,873 | A | 7/1996 | Debabov et al. |
| 5,631,157 | A | 5/1997 | Debabov et al. |
| 5,658,766 | A | 8/1997 | Livshits et al. |
| 5,705,371 | A | 1/1998 | Debabov et al. |
| 5,976,843 | A | 11/1999 | Debabov et al. |
| 6,132,999 | A | 10/2000 | Debabov et al. |
| 6,165,756 | A | 12/2000 | Debabov et al. |
| 6,297,031 | B1 | 10/2001 | Debabov et al. |
| 6,303,348 | B1 | 10/2001 | Livshits et al. |

FOREIGN PATENT DOCUMENTS

EP          0 519 113         12/1992

OTHER PUBLICATIONS

Burkovski et al. Bacterial amino acid transport proteins: occurrence, functions, and significance for biotechnological applications. Appl. Microbiol Biotechnol. Mar.2002; 58(3):265–74.*

H. Tsunekawa, et al., Applied and Environmental Microbiology, vol. 58, No. 6, pp. 2081–2088, "Acquisition of a Sucrose Utilization System in *Escherichia Coli* K–12 Derivatives and its Application to Industry", Jun. 1992.

K. Schmid, et al., Molecular Microbiology, vol. 2, No. 1 pp. 1–8, "Plasmid–Mediated Sucrose Metabolism in *Escherichia coli* K12: Mapping of The scr Genes of pUR400", 1988.

J. L. Garcia, Molecular & General Genetics, vol. 201, No. 3, pp. 575–577, "Cloning in *Escherichia Coli* and Molecular Analysis of the Sucrose System of the *Salmonella* Plasmid SCR–53", 1985.

J. Bockmann, et al., Molecular and General Genetics, vol. 235, No. 1, pp. 22–32, "Characterization of a Chromosomally Encoded, Non–PTS Metabolic Pathway for Sucrose Utilization in *Escherichia coli* EC3132", Oct. 1, 1992.

Derwent Abstract of Research Disclosure, AN 2000–439902 (38), vol. 433, No. 020, 2 pages, "Fermentative Production of Amino Acids and Vitamins, Useful E.G. in Medicine, By Growing *Escherichia coli* that Includes the Chromosomally Coded Sucrose System", May 10, 2000.

Debabov V., "Construction of strains producing L–threonine", Proceedings of the IVTH International Symposium on Genetics of Industrial Microorganisms, 1982, pp 254–258.

* cited by examiner

*Primary Examiner*—Kathleen Kerr
(74) *Attorney, Agent, or Firm*—Cermak & Kenealy, LLP; Shelly Guest Cermak

(57) ABSTRACT

An amino acid such as threonine, homoserine, isoleucine, lysine, valine and tryptophan is produced using a bacterium belonging to the genus *Escherichia* which has been constructed from sucorse non-assimilative strain belonging to the genus *Escherichia* and which harbors sucrose non-PTS (phosphoenol pyruvate-dependent sucrose-6-phosphotransferase system) genes and has an ability to produce the amino acid.

2 Claims, 4 Drawing Sheets

METHODS OF MAKING AMINO ACIDS USING E. COLI TRANSFORMED WITH CSC GENES

BACKGROUND OF THE INVENTION

1. Field of the Invention

The present invention relates to biotechnology and, more specifically, to a method for producing amino acids by fermentation using amino acid producing bacterium belonging to the genus Escherichia capable of utilizing sucrose a sole carbon source.

2. Description of the Related Art

Sucrose and sucrose containing substrates (e.g. molasses) are often used as a starting point for the microbial production of commercial products such as amino acids, vitamins and organic acids. The process for production of amino acids from carbohydrates strives to maximize the efficiency with which the carbon skeleton of carbohydrate is converted into desired product.

The majority of sucrose-positive bacteria take up and phosphorylate sucrose by a phosphoenol pyruvate-dependent, sucrose-6-phosphotransferase system (sucrose PTS) to yield intracellular sucrose-6-phosphate. This phosphate is hydrolyzed by a sucrose-6-phosphate hydrolase (invertase or sucrase) into D-glucose 6-phosphate and D-fructose, which is itself phosphorylated by an ATP-D-fructose-6-phosphate phosphotransferase (fructokinase). Such systems and metabolic pathways have been described at the molecular level for the gram-positive bacteria *Bacillus subtilis* and *Streptococcus mutans* (Debarbouille et al., 1991. *Res. Microbiol.*, 142: 757–764; Sato et al., 1989. *J. Bacteriol.*, 171: 263–271) and for gram-negative bacteria. Further plasmid-coded pUR400 system from enteric bacteria has been reported (Aulkemeyer et al., (1991) *Mol. Microbiol.*, 5: 2913–2922; Schmid et al., 1988. *Mol. Microbiol.*, 2: 1–8; Schmid et al., 1991. *Mol. Microbiol.*, 5: 941–950).

Although about 50% of wild-type isolates of *Escherichia coli* are sucrose positive, the laboratory *E. coli* strains such as *E. coli* K-12, *E. coli* B, *E. coli* C which are now used in the breeding of the industrially important producing strains cannot utilize sucrose. However, this property may be easily provided to these strains by introducing sucrose utilization genes from sucrose-positive *E. coli* or *Salmonella* strains using conjugation, transduction or cloning procedures (Wohlhieter et al., 1975. *J. Bacteriol.*, 122:401–406; Parsell and Smith, 1975. *J. Gen. Microbiol.*, 87: 129–137; Alaeddinoglu and Charles, 1979. *J. Gen. Microbiol.*, 110:47–59; Livshits et al., 1982. In: Metabolic plasmids. P.132–134; Garsia, 1985. *Mol. Gen. Genet.*, 201:575–577; U.S. Pat. No. 5,175,107).

Phosphoenol pyruvate (PEP) is one of the major building blocks in several biosynthetic pathways. PEP is combined with carbon dioxide to produce oxaloacetic acid. Oxaloacetic acid serves as the carbon skeleton for aspartic acid, asparagine, threonine, isoleucine, methionine and lysine. Besides, an equimolar amount PEP is condensed with erythrose-4-phosphate to form 3-deoxy-D-arabino-heptulosonate 7-phosphate (DAHP), the first intermediate of the common segment of the aromatic pathway. From this metabolic route such commercially important amino acids as tryptophan, phenylalanine and tyrosine can be obtained. The yield of these metabolites may be limited by PEP availability.

During glycolysis four moles of PEP are produced from two mole of glucose, and half of the PEP is obligatory consumed to provide energy for glucose uptake. In the case of sucrose internalization two moles of hexose (glucose and fructose) arising from one mole of sucrose also produce four moles of PEP, but only one mole is consumed for the sucrose transport, thus increasing 1.5 times the amount of PEP available as a source of carbon skeletons for biosynthesis. Therefore, it is possible to improve the amino acid yield by providing the *E. coli* amino acid producing strains with the ability to utilize sucrose, and using sucrose or sucrose containing substrates as a carbon source.

Known in the present state of the art is the threonine producing strain VKPM B-3996 based on *E. coli* K-12 capable of sucrose utilization (U.S. Pat. No. 5,705,371). The restriction and sequence analysis of the cloned sucrose genes from the VKPM B-3996 strain showed that they are almost identical to those of pUR400 (accession numbers: EMBL X61005; EMBL X67750, GB M38416) encoding PTS sucrose transport and metabolism (Lengeler et al., 1982. *J. Bacteriol.*, 151:468–471; Schmid et al., 1988, *Mol. Microbiol.*, 2:1–8; Schmid et al., 1991, *Mol. Microbiol.*, 5:941–950).

A chromosomally encoded, non-PTS metabolic pathway for sucrose utilization was also found in *Escherichia coil* (Bockmann et al., 1992, *Mol. Gen. Genet.*, 235:22–32). The pathway involves a proton symport transport system (LacY type permease), an invertase, a fructokinase, and a sucrose-specific repressor. By using this non-PTS metabolic pathway the output of an amino acid derived from a PEP precursor could be further increased because sucrose transport into the cells would not be coupled to PEP. However this approach was never used before for the amino acid producing strain improvement.

SUMMARY OF THE INVENTION

It is an object of the present invention to provide a method for producing amino acids using *Escherichia coli* strains containing the genes encoding metabolic pathway for sucrose utilization, especially non-PTS metabolic pathway for sucrose utilization.

The inventors have found that a bacterium belonging to the genus *Escherichia* having amino acid productivity produces the amino acid efficiently by introducing sucrose genes into the bacterium. Thus the present invention have completed.

That is the present invention provides:

(1) A bacterium belonging to the genus *Escherichia* which has been constructed from a sucrose non-assimilative strain belonging to the genus *Escherichia*, the bacterium harboring sucrose PTS genes and having an ability to produce an amino acid other than threonine.

(2) The bacterium according to (1), wherein the bacterium belonging to the genus *Escherichia* is *Escherichia coli*.

(3) The bacterium according to (1) or (2), wherein the amino acid is selected from the group consisting of homoserine, isoleucine, lysine, valine and tryptophan.

(4) A bacterium belonging to the genus *Escherichia* which has been constructed from a sucorse non-assimilative strain belonging to the genus *Escherichia*, the bacterium harboring sucrose non-PTS genes and having an ability to produce an amino acid.

(5) The bacterium according to (4), the sucrose non-PTS genes comprising at least genes coding for a proton symport transport system, invertase and fructokinase.

(6) The bacterium according to (4) or (5), wherein the bacterium belonging to the genus *Escherichia* is *Escherichia coli*.

(7) The bacterium according to any of (4) to (6), wherein the amino acid is selected from the group consisting of threonine, homoserine, isoleucine, lysine, valine and tryptophan.

(8) A method for producing an amino acid comprising the steps of cultivating the bacterium according to any one of (1) to (7) in a culture medium to produce and accumulate the amino acid in the culture medium, and collecting the amino acid from the culture medium.

In the present invention, an amino acid is of L-configuration unless otherwise noted.

The present invention will be explained in detail below.

The bacterium belonging to the genus *Escherichia* of the present invention is a strain which is constructed from sucrose non-assimilative *Escherichia coli* as a parent strain, and which harbors sucrose genes, especially sucrose non-PTC genes, and has an ability to produce amino acid.

A sucrose non-assimilative *Escherichia coli* is not particularly limited so long as it has an ability to produce an amino acid or it can be conferred the ability. The examples of such strains includes *E. coli* K-12, *E. coli* B and *E. coli* C, and their derivative strains, more concretely, the amino acid producing strains mentioned later.

The bacterium of the present invention may be obtained by introduction of sucrose PTS genes or sucrose non-PTS genes into an amino acid producing strain such as the above strains. Alternatively, the bacterium of the present invention may be obtained by conferring an ability to produce an amino acid to a bacterium belonging to the genus *Escherichia* in which sucrose PTS genes or sucrose non-PTS genes are introduced.

Sucrose non-PTS genes are not particularly limited so long as they can function in a bacterium belonging to the genus *Escherichia*. The genes, for example, exemplified by the sucrose non-PTS genes (csc) harbored by *E. coli* EC3132 (Bockmann et al., 1992. *Mol. Gen. Genet.*, 235:22–32). The csc genes may be prepared from *E. coli* K-12 W3350csc. The strain W3350csc has been deposited in Russian National Collection of Industrial Microorganisms (Russia 113545 Moscow 1 Dorozhny proezd, 1) based on Budapest Treaty under the accession number of VKPM B-7914.

The csc genes includes the genes coding for a proton symport transport system (LacY type permease), invertase, fructokinase, and sucrose-specific repressor. Among these, the present invention requires at least the genes coding for permease, invertase and fructokinase.

An amino acid can be also produced efficiently by introduction of sucrose PTS into a bacterium belonging to the genus *Escherichia*. As the sucrose PTS genes may be exemplified by scr genes included in pUR400 system encoded by the plasmid derived from the enteric bacterium (Aulkemeyer et al. (1991) *Mol. Microbiol.*, 5: 2913–2922; Schmid et al., 1988, *Mol. Microbiol.*, 2:1–8; Schmid et al., 1991, *Mol. Microbiol.*, 5:941–950). Alternatively, the sucrose PTS genes may be prepared from the transposon Tn2555 (Doroshenko et al., 1988, *Molec. Biol.*, 22:645–658).

The sucrose non-PTS genes and PTS genes can be incorporated into a bacterium belonging to the genus *Escherichia* by, for example, introducing a recombinant plasmid containing the desired genes into the bacterium. Specifically, the desired genes can be incorporated into a bacterium belonging to the genus *Escherichia* by introduction of a plasmid, a phage or a transposon (Berg, D. E. and Berg, C. M., Bio/Technol., 1, 417 (1983)) which carries the desired genes into a cell of the bacterium.

The vector is exemplified by plasmid vectors such as pBR322, pMW118, pUC19 or the like, and phage vectors including P$_1$vir phage, mini-Mud such as pMu4041 or the like. The transposon is exemplified by Mu, Tn10, Tn5 or the like.

The introduction of a DNA into a bacterium belonging to the genus *Escherichia* can be performed, for example, by a method of D. A. Morrison (Methods in Enzymology 68, 326 (1979)) or a method in which recipient bacterial cells are treated with calcium chloride to increase permeability of DNA (Mandel, M. and Higa, A., *J. Mol. Biol.*, 53, 159 (1970)) and the like. Alternatively, the introduction of a DNA can be also performed by transduction using a phage vector.

The sucrose non-PTS genes or PTS genes are introduced into amino acid producing bacterium belonging to the genus *Escherichia* with the result that the amino acid is produced from sucrose. As the bacterium belonging to the genus *Escherichia* to which the sucrose non-PTS genes or PTS genes are introduced, strains which have a productivity of desired amino acid may be used. Besides, amino acid productivity may be conferred to a bacterium to which the sucrose non-PTS genes or PTS genes are introduced. Examples of amino acid producing bacteria belonging to the genus *Escherichia* are described below.

(1) Threonine Producing Bacteria

As threonine producing bacteria belonging to the genus *Escherichia*, there may be exemplified MG442 (referred to Gusyatiner et al., *Genetika* (in Russian), 14, 947–956 (1978)), VL643 and VL2055 (see Examples 2 and 3).

(2) Homoserine Producing Bacteria

*E. coli* NZ10 and NZ10rhtA23/pAL4 may be exemplified as homoserine producing bacteria belonging to the genus *Escherichia*. The strain NZ10 was obtained as a Leu$^+$ revertant of a known strain C600 (Appleyard R. K., *Genetics*, 39, 440–452 (1954)). The strain NZ10rhtA23/pAL4 which was constructed from NZ10 (see Example 4).

(3) Isoleucine Producing Bacteria

As isoleucine producing bacteria, there may be exemplified *E. coli* 44-3-15 srtain, KX141 strain (VKPM B-4781) (EP-A-519113), and TDH-6/pVIC40, pMWD5 (WO97/08333) are exemplified.

(4) Lysine Producing Bacteria

As lysine producing bacteria, *E. coli* VL612 is preferable (Example 5). Additionally, there may be exemplified lysine producing bacteria belonging to the genus *Escherichia*, concretely a mutant strain having resistance to lysine analogues. The lysine analog is such one which inhibits proliferation of bacteria belonging to the genus *Escherichia*, but the suppression is entirely or partially desensitized if lysine coexists in a medium. For example, there are oxalysine, lysine hydroxamate, (S)-2-aminoethyl-L-cysteine (AEC), gamma-methyllysine, chlorocaprolactam and the like. Mutant strains having resistance to these lysine analogues are obtained by applying an ordinary artificial mutation operation to bacteria belonging to the genus *Escherichia*. The bacterial strain to be used for lysine production is concretely exemplified by *Escherichia coli* AJ11442 (deposited as FERM BP-1543 and NRRL B-12185; see Japanese Patent Laid-open No. 56–18596 or U.S. Pat. No. 4,346,170) and *Escherichia coli* VL611. *Escherichia coli* AJ11442 was deposited in National Institute of Bioscience and Human Technology, Agency of Industrial Science and Technology (currently National Institute of Bioscience and Human Technology, National Institute of Advanced Industrial Science and Technology)(postal code: 305, 13, Higashi 1 chome, Tsukubashi, Ibarakiken, Japan) on May 5, 1981 under a deposition number of FERM P-5084, and transferred from the original deposition to international deposition based on Budapest Treaty on Oct. 29, 1987, and has been deposited as deposition number of FERM BP-1543. In aspartokinase of the microorganisms described above, feedback inhibition by lysine is desensitized.

Besides, for example, threonine producing bacteria are exemplified, because inhibition of their aspartokinase by lysine is generally desensitized also in the threonine producing microorganisms. As an threonine producing bacterium belonging to *E. coli*, MG442 (Gusyatiner, et al., *Genetika* (in Russian), 14, 947–956 (1978) is exemplified.

Gene(s) encoding the enzyme(s) in the lysine biosynthesis may be enhanced in the above mentioned bacterium. For example, such a gene is exemplified by the gene encoding phosphoenolpyruvate carboxylase which is mutated to be desensitized to the feedback inhibition by aspartic acid (see Japanese Patent Publication No. 7-83714).

(5) Valine Producing Bacteria

Valine producing bacteria are concretely exemplified by *E. coli* VL1970 (VKPM B-4411)(see EP-A-519113) and VL1971 (see Example 6). Besides, bacteria belonging to the genus *Escherichia* which carry the genes for the biosynthesis of valine of which the regulatory mechanism is substantially suppressed are exemplified. Such bacteria may be obtained by introduction of the ilvGMEDA operon, which does not preferably express threonine deaminase and of which attenuation is suppressed, into bacteria belonging to the genus *Escherichia* (Japanese Patent Laid-Open Publication No. 8-47397).

The ilvGMEDA operon can be obtained from *E. coli* chromosomal DNA by colony hybridization or PCR using oligonucleotide which is prepared according to the nucleotide sequence of the operon, whose entire sequence is disclosed (*Nucleic Acid Res.*, 15, 2137 (1987)). Introduction of DNA fragment including the ilvGMEDA operon can be performed by the method using plasmid, phage or transposon as described above.

(6) Tryptophan Producing Bacteria

An tryptophan producing bacterium is concretely exemplified by *E. coli* SV164(pGH5)(see Example 7), AGX17 (pGX44) (NRRL B-12263) and AGX6(pGX50)aroP(NRRL B-12264) (USP 4,371,614), AGX17/pGX50, pACKG4-pps (WO97/08333).

(7) Phenylalanine Producing Bacteria

A phenylalanine producing bacterium is exemplified by *E. coli* AJ 12604 (FERM BP-3579)(EP-A-488424).

An amino acid can be efficiently produced from sucrose by cultivating the bacterium described above, into which the sucrose non-PTS genes or PTS genes are introduced and which has an ability to produce an amino acid, in a culture medium containing sucrose, to produce and accumulate the amino acid in the medium, and collecting the amino acid from the medium. The amino acid is exemplified preferably by threonine, homoserine, isoleucine, lysine, valine, tryptophan, tyrosine, phenylalanine and methionine, more preferably by threonine, homoserine, isoleucine, lysine, valine, tryptophan.

In the method for producing amino acids of present invention, the cultivation of the bacterium belonging to the genus *Escherichia*, the collection and purification of amino acid from the liquid medium may be performed in a manner similar to the conventional fermentation method wherein an amino acid is produced using a bacterium. A medium used in culture may be either a synthetic medium or a natural medium, so long as the medium includes a carbon and a nitrogen source and minerals and, if necessary, a moderate amount of nutrients which the bacterium used requires for growth. As a main carbon source, sucrose is used. Small amount of carbon sources other than sucrose may be contained in the medium as an auxiliary carbon source. As the nitrogen source, various ammonium salts such as ammonia and ammonium sulfate, other nitrogen compounds such as amines, a natural nitrogen source such as peptone, soybean hydrolyte and digested fermentative microbe are used. As minerals, potassium phosphate, magnesium sulfate, sodium chloride, ferrous sulfate, manganese sulfate, calcium carbonate are used.

The cultivation is performed preferably under aerobic conditions such as a shaking culture, and an aeration and stirring culture, at a temperature of 20–40° C., preferably between 30° C. and 38° C. The pH of the culture is usually between 5 and 9, preferably between 6.5 and 7.2. The pH of the culture can be adjusted with ammonia, calcium carbonate, various acids, various bases, and buffers. Usually, 1 to 3 day cultivation leads to the accumulation of the target amino acid in the liquid medium.

After cultivation, solids such as cells are removed from the liquid medium by centrifugation and membrane filtration, and then the target amino acid can be collected and purified by ion-exchange, concentration and crystalline fraction methods.

BEST MODE FOR CARRYING OUT THE INVENTION

Hereafter, the present invention will be further specifically explained with reference to the following examples.

EXAMPLE 1

Preparation of the Donor of Sucrose Non-PTS Genes and PTS Genes (1) Sucrose PTS Genes The strain VD1 was used as a donor of PTS sucrose utilization (scr) genes. This strain was obtained as follows. The transposon Tn2555 carries the scr genes (Doroshenko et al., 1988. *Molec. Biol.*, 22:645–658). The restriction analysis and partial sequencing revealed that the scr genes of Tn2555 are identical to those of pUR400 (accession numbers: EMBL X61005; EMBL X67750, GB M38416) that control sucrose transport and metabolism via PTS system.

The scr genes of Tn2555 were cloned into pM1, a mini-Mud vector pMu4041 derivative, obtained by the deletion of Mu-phage genes encoding transposase and repressor (M. Faelen. Useful Mu and mini-Mu derivatives. In: Phage Mu. Symonds et al., eds. Cold Spring Harbor Laboratory, New York, 1987, pp.309–316). This was performed in two steps. At the first step the SspI fragment of pBRS5.2 (pBR325::Tn2555) (Doroshenko et al., 1988. *Molec. Biol.* 22: 645–658) containing scrYABR genes and only a part of scrK gene was inserted into the PvuII-restricted pM1 replacing the kan gene.

Figure 1:
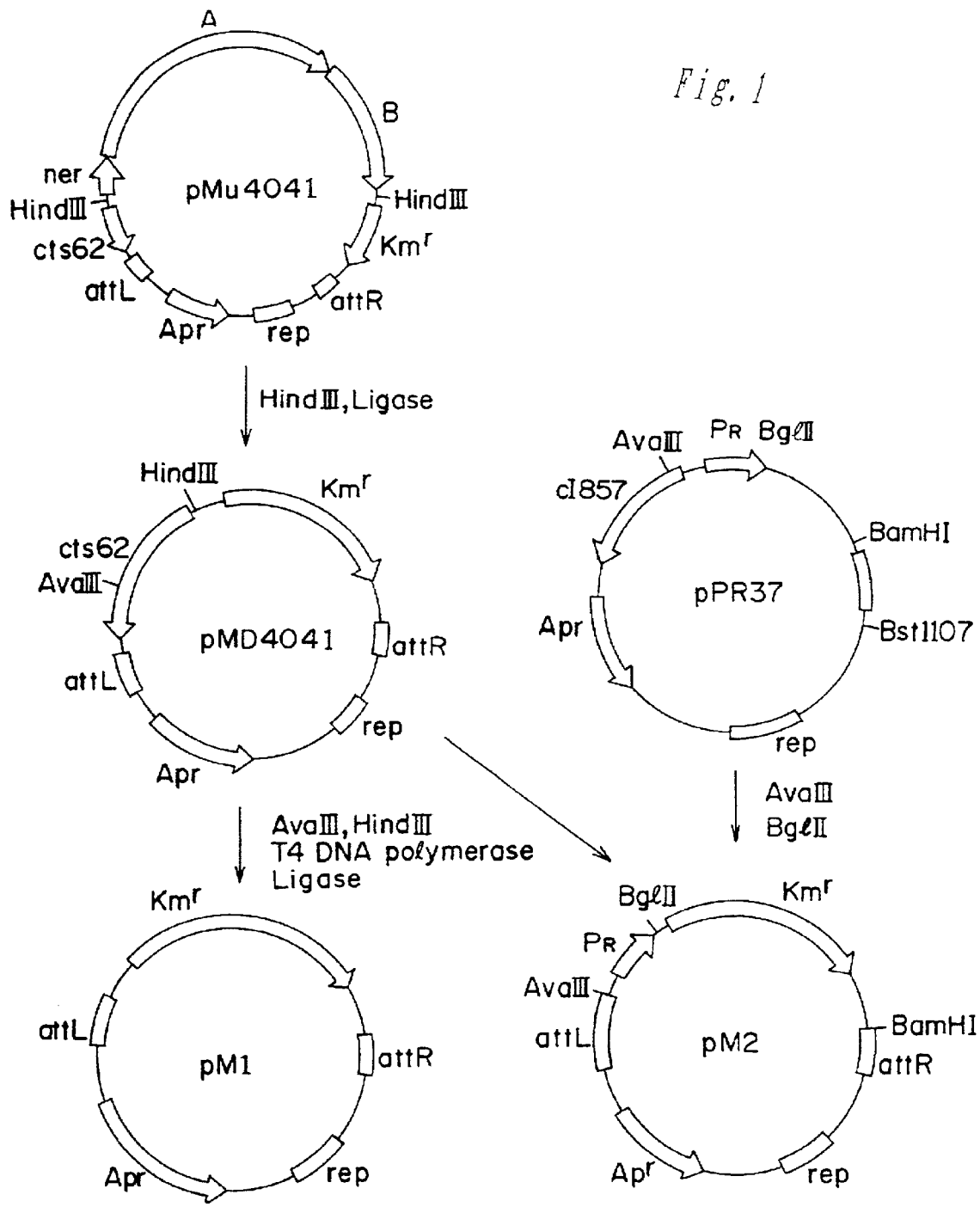
FIG. 1 shows the construction of the plasmids pM1 and pM2 which are derivatives of mini-Mud 4041.

The above plasmid pM1 was obtained as follows (FIG. 1). The plasmid pMu4041 was digested with HindIII and re-circularized to excise gene A, B encoding transposase of phage Mu and the ner gene encoding negative regulator, and a plasmid pMD4041 was obtained. Then pMD4041 was digested with AvaIII and HindIII, and blunt-ended with T4 DNA polymerase followed by recirculization to remove cts62 phage Mu repressor.

Figure 2:
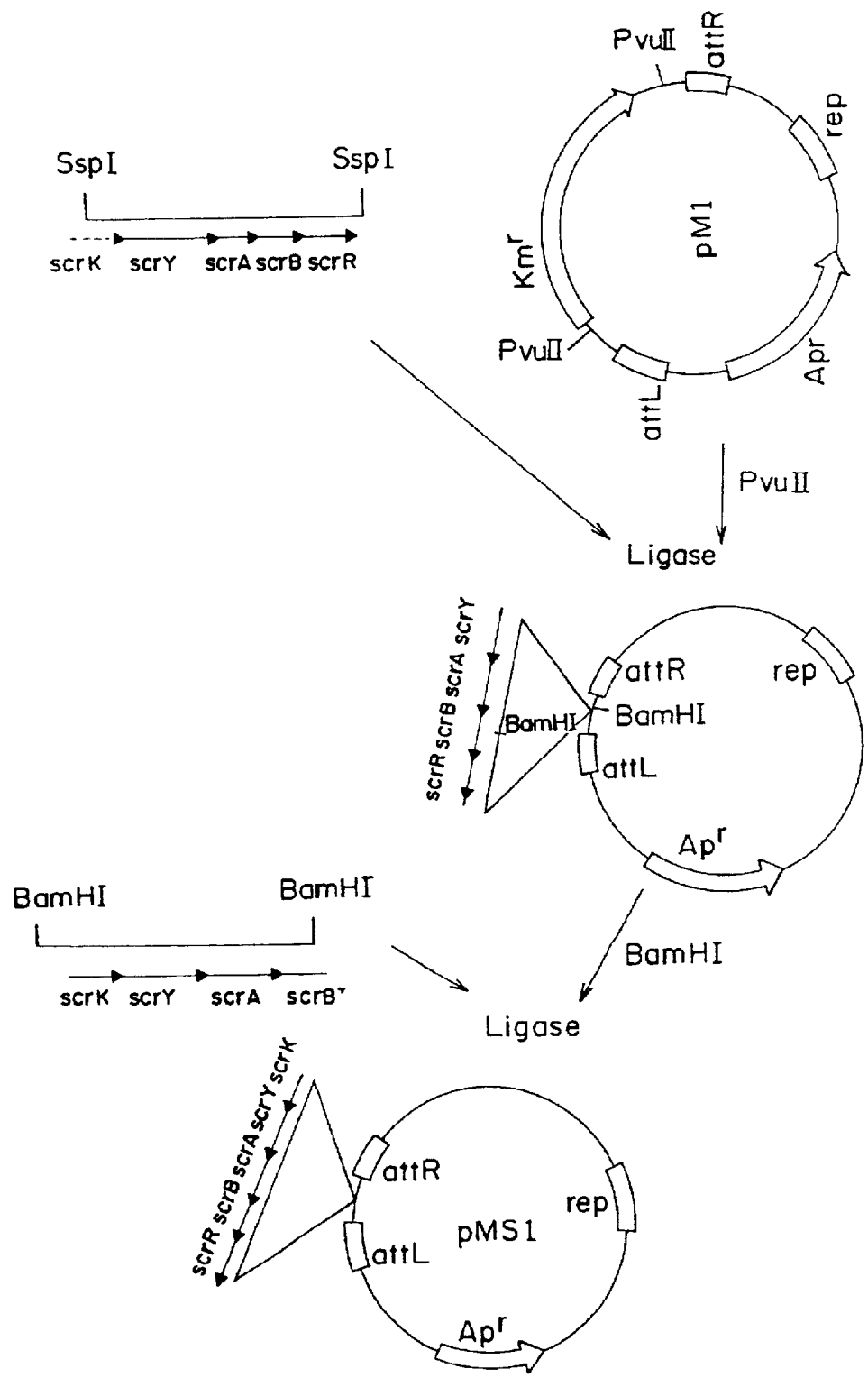
FIG. 2 shows the scheme for cloning of the scr genes in pM1.

At the second step, BamHI fragment of the resulted plasmid was substituted for the BamHI fragment of pBRS5.2, restoring the scrK gene. Thus the whole sucrose cluster of Tn2555 was cloned into the plasmid containing also $amp^R$ marker and phage Mu ends. This plasmid, marked as pMS1, contains transposable mini-Mu-scrKYABR DNA fragment (FIG. 2).

To integrate mini-Mu-scrKYABR into the bacterial chromosome standard procedure was used. pMS1 was introduced into the cells of MG1655(pMH10). Mu transposase encoded by pMH10 (pACYC177 derivative harboring $Km^R$ gene, Mu-phage A and B genes encoding Mu transposase, cts62 gene encoding Mu repressor, and the phage-lambda repressor gene cI857) was induced by 15 min incubation at 42° C. immediately after the transformation. Sucrose-positive ($Scr^+$) clones were selected on M9 agar plates containing 0.2% sucrose as a sole carbon source at 30° C., washed out and incubated in LB-broth (J. Miller. Experiments in molecular genetics. Cold Spring Harbor laboratory, New York, 1972) containing no antibiotics for 48–72 h. Then the appropriate dilutions of the culture broth were plated on M9 agar plates containing 0.2% sucrose. Several tens of $Amp^S$, $Km^S$ clones were picked up and tested. It proved that they did not contain plasmids. Among them the strain VD1 (MG1655::mini-Mu-scrKYABR) was selected which is a prototrophic fast-growing sucrose-positive strain.

Besides, the strain VL478, harboring the pVG478 plasmid containing sucrose genes in the Tn2555 transposon (*Molecular Genetics, Microbiology and Virology*, No. 6, 23–28 (1987)) was also used as a donor of scr genes. Strain VL478 have been deposited in the Russian National Collection of Industrial Microorganisms (VKPM) under the accession number VKPM B-7915.

Above strains were used as donors of SCR genes in the following Examples.

(2) Sucrose Non-PTS Genes

As a source of non-PTS sucrose utilization (csc) genes the strain of *E. coli* K12 W3350csc was used. This strain contains csc genes of *E. coli* EC3132 (Bockmann et al., 1992. Mol.Gen.Genet., 235:22–32). Strain W3350csc have been deposited in the Russian National Collection of Industrial Microorganisms (VKPM) under the accession number VKPM B-7914. The csc genes contain genes coding for permease, fructokinase, invertase and repressor.

EXAMPLE 2

Preparation of the *E. coli* Threonine Producing Strain Capable to Utilize Sucrose and Threonine Production Using the Strain (1)

As a recipient strain to which the PTS genes were introduced, *E. coli* VL643 was newly constructed as follows.

The known strain *E. coli* MG442 (Guayatiner et al., *Genetika* (in Russian), 14, 947–956 (1978), VKPM B-1628) was transduced the rhtA23 mutation from the strain 472T23/pYN7 (VKPM B-2307) to obtain VL643 strain. The rhtA23 is a mutation which confers resistance to high concentration of threonine (>40 mg/ml) or homoserine (>5 mg/ml), and improves threonine production (ABSTRACTS of 17th International Congress of Biochemistry and Molecular Biology in conjugation with 1997 Annual Meeting of the American Society for Biochemistry and Molecular Biology, San Francisco, Calif. Aug. 24–29, 1997, abstract No. 457).

Thus obtained threonine-producing strain VL643 was infected with phage $P1_{vir}$ grown on the donor strain VL478. The transductants were selected on M9 minimal medium containing 0.2% sucrose as a sole carbon source. Thus the strains VL644 was obtained. This strain and the parent strain were each cultivated at 37° C. for 18 hours in a nutrient broth, and 0.3 ml of each of the obtained cultures was inoculated into 3 ml of a fermentation medium having the following composition in a 20×200 mm test tube, and cultivated at 37° C. for 72 hours with a rotary shaker.

| Fermentation medium composition (g/L): | |
|---|---|
| Sucrose (or Glucose) | 50.0 |
| $(NH_4)_2SO_4$ | 10.0 |
| $K_2HPO_4$ | 1.0 |
| NaCl | 1.0 |
| $MgSO_4 * 7H_2O$ | 0.8 |
| $FeSO_4 * 7H_2O$ | 0.02 |
| $MnSO_4 * 5H_2O$ | 0.02 |
| Thiamine hydrochloride | 0.002 |
| $CaCO_3$ | 20 |

($MgSO_4 * 7H_2O$ and $CaCO_3$ were each sterilized separately).

After the cultivation, an accumulated amount of threonine in the medium and an absorbance at 560 nm of the medium were determined by known methods. The results are presented in Table 1.

TABLE 1

| | Glucose | | | Sucrose | | |
|---|---|---|---|---|---|---|
| Strain | $OD_{560}$ | Threonine (g/l) | Yield (%) | $OD_{560}$ | Threonine (g/l) | Yield (%) |
| VL643 | 10.1 | 7.0 | 14.0 | — | — | — |
| VL644 | 9.9 | 7.2 | 14.4 | 10.5 | 9.7 | 19.4 |

As shown in Table 1, both strains, VL643 and VL644, grew equally in medium with glucose and accumulated about the same amount of threonine. Besides, the strain VL644 grew well in medium with sucrose and accumulated under this condition more threonine with a higher yield.

EXAMPLE 3

Preparation of the *E. coli* Threonine Producing Strain Capable to Utilize Sucrose and Threonine Production Using the Strain (2)

As a recipient strain to which the PTS genes were introduced, *E. coli* VL2055 was constructed.

*E. coli* VL2055 was derived from the known *E. coli* strain VKPM B-3996 (U.S. Pat. No. 5,705,371). The strain B-3996, of which host strain is *E. coli* TDH-6, is deficient in thrC gene and is sucrose-assimilative, in which ilva gene has a leaky mutation. The strain B-3996 harbors the plasmid pVIC40 which had been obtained by inserting thrA*BC operon including thrA* gene encoding AKI-HDI which was substantially desensitized inhibition by threonine into RSF1010-derived vector.

From the strain B-3996, VL2055 was constructed in the following two steps.

Initially the plasmidless derivative of the strain VKPM B-3996, TDH-6, was selected after spontaneous elimination of pVIC40 plasmid. Next, a mutation inactivating kan gene of the Tn5 transposon inserted into the tdh gene of TDH-6 was obtained by known method (NTG mutagenesis). Then sucrose non-utilizing derivative of the resulted strain was selected after elimination of genetic determinants of sucrose assimilation. Thus the strain VL2053 was obtained.

Figure 3:
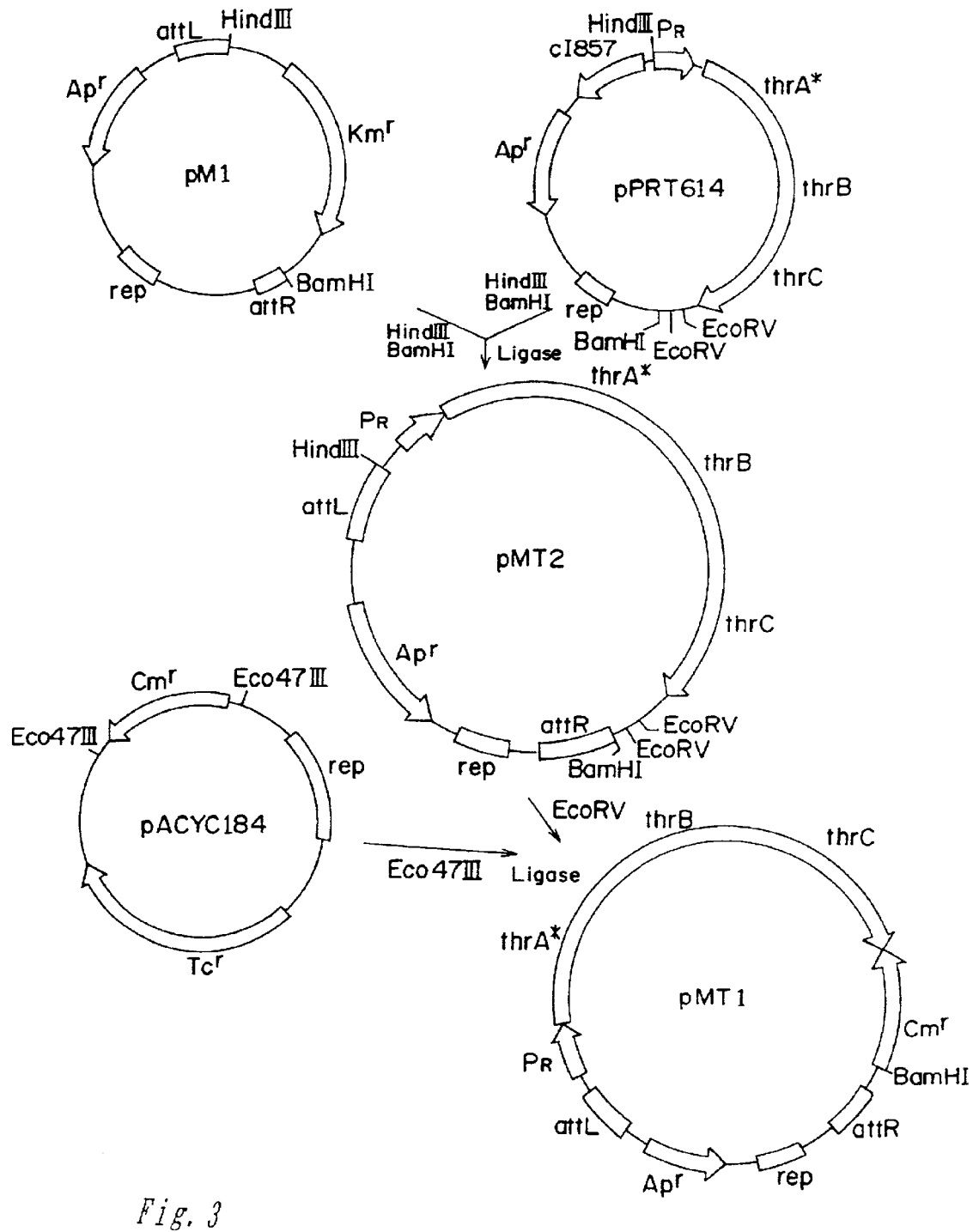
FIG. 3 shows the construction of the plasmids pMT1 and pMT2.

On the other hand, the plasmid pPRT614 (EP 0593792) which is harbored by *E. coli* VKPM B-5318 was digested with HindIII and BamHI to excise the fragment containing the threonine operon under lambda-phage $P_R$ promoter. The threonine operon contains mutation in thrA gene (thrA*), which confers aspartokinase-homoserine dehydrogenase I insensitivity to feedback inhibition by threonine. The obtained fragment was cloned into pM1, a mini-Mud vector pMu4041 derivative (M.Faelen. Useful Mu and mini-Mu derivatives. In: Phage Mu. Symonds et al., eds. Cold Spring Harbor Laboratory, New York, 1987, pp.309–316) to obtain the plasmid pMT2 (FIG. 3).

In addition, the cat gene of Tn9 from pACYC184 conferring the resistance to chloramphenicol was cloned into pMT2. Thus the plasmid pMT1 containing a transposable construct of $P_R$-thrA*BC and cat genes flanked by Mu ends (mini-Mu-thrA*BC-cat) was obtained (FIG. 3).

Figure 4:
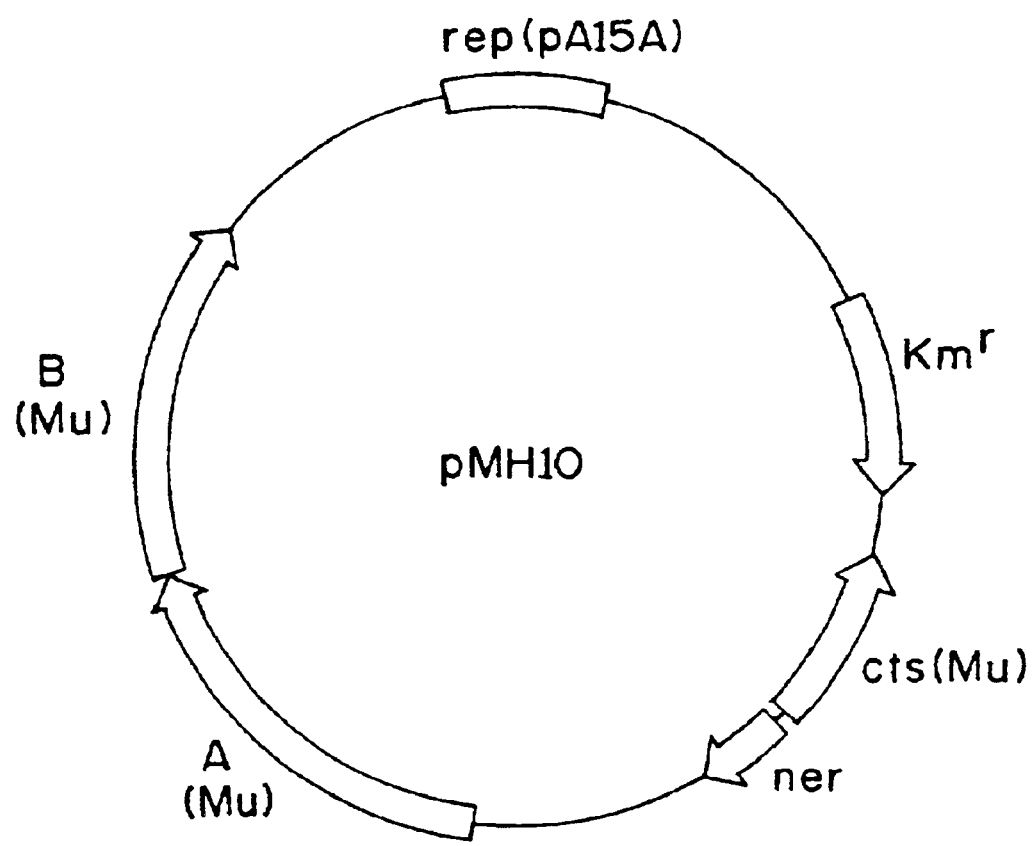
FIG. 4 shows the conformation of the plasmid pMH10 which harbors $Km^R$ gene, Mu-phage A and B genes encoding Mu transposase, the ner gene encoding negative regulator, and cts62 gene encoding Mu repressor.

This plasmid was introduced into the cells of *E. coli* C600(pMH10). Mu transposase encoded by pMH10 (pACYC177 derivative harboring $Km^R$ gene, Mu-phage A and B genes encoding Mu transposase, the ner gene encoding negative regulator, and cts62 gene encoding Mu repressor, see FIG. 4) was induced by 15 min incubation at 42° C. immediately after the transformation.

Chloramphenicol resistant ($Cm^R$) clones were selected on LB agar plates containing 15 mg/l chloramphenicol at 30° C. Several tens of $Km^S$ clones were picked up and tested. It proved that most of them did not contain plasmids. Then the PR-thrA*BC-cat genes from the chromosome of one of the selected C600 Thr+, $Cm^R$ strain were transduced by the use of $P1_{vir}$ into the strain VL2053, obtained at the first step, giving the new plasmidless threonine producing strain VL2055.

The threonine-producing strain VL2055 was infected with phage $P1_{vir}$ grown on the donor strains VD1 or W3350csc. The transductants were selected on M9 minimal medium containing 50 mg/l isoleucine and 0.2% sucrose as a sole carbon source. Thus the strains VL2055 Scr and VL2055 Csc, respectively, were obtained. These strains and the parent strain were each cultivated at 37° C. for 18 hours in a nutrient broth, and 0.3 ml of the obtained culture was inoculate into 3 ml of a fermentation medium having the following composition in a 20×200 mm test tube, and cultivated at 37° C. for 72 hours with a rotary shaker.

| Fermentation medium composition (g/L): | |
| --- | --- |
| Sucrose (or Glucose) | 80 |
| Isoleucine | 0.1 |
| (NH$_4$)$_2$SO$_4$ | 22 |
| K$_2$HPO$_4$ | 2 |
| NaCl | 0.8 |
| MgSO$_4$ * 7H$_2$O | 0.8 |
| FeSO$_4$ * 7H$_2$O | 0.02 |
| MnSO$_4$ * 5H$_2$O | 0.02 |
| Thiamine hydrochloride | 0.2 |
| Yeast Extract | 1.0 |
| CaCO$_3$ | 30 |

(MgSO$_4$ * 7H$_2$O and CaCO$_3$ each were sterilized separately)

After the cultivation, an accumulated amount of threonine in the medium and an absorbance at 560 nm of the medium were determined by known methods. The results are presented in Table 2.

TABLE 2

| | Glucose | | | Sucrose | | |
| --- | --- | --- | --- | --- | --- | --- |
| Strain | OD$_{560}$ | Threonine (g/l) | Yield (%) | OD$_{560}$ | Threonine (g/l) | Yield (%) |
| VL2055 | 12.0 | 18.9 | 23.6 | — | — | — |
| VL2055 scr | 11.7 | 19.5 | 24.4 | 11.4 | 23.3 | 29.1 |
| VL2055 csc | 11.6 | 19.2 | 24.0 | 11.6 | 27.9 | 34.9 |

As shown in Table 2, both sucrose utilizing strains, VL2055 Scr and VL2055 Csc, had the same growth characteristics and accumulated about the same amount of threonine as their parent VL2055 when cultured in glucose-containing medium. However, these strains accumulated more threonine with a higher yield when cultured in sucrose-containing medium. Besides, the VL2055 Csc strain (having sucrose non-PTS genes) was more productive under this condition than the VL2055 Scr strain (having sucrose PTS genes).

EXAMPLE 4

Preparation of the *E. coli* Homoserine Producing Strain Capable to Utilize Sucrose, and Homoserine Production Using This Strain As a recipient strain producing homoserine to which the PTS genes were introduced, *E. coli* NZ10 rhtA23/pAL4 was constructed by derivation from the strain NZ10. The strain NZ10 (thrB) is a leuB+-revertant obtained from the *E. coli* strain C600 (thrB, leuB) (Appleyard R. K., *Genetics*, 39, 440–452 (1954)). Then the rhtA23 mutation was introduced as described in Example 2, giving the NZ10 rhtA23 strain. This strain was transformed with the pAL4 plasmid which was a pBR322 vector into which the thrA gene coding for aspartokinase-homoserine dehydrogenase I was inserted.

The homoserine-producing strain NZ10 rhtA23/pAL4 was infected with the phage $P1_{vir}$ grown on the donor strain VD1. The transductants were selected on M9 minimal medium containing 0.2% sucrose and 50 mg/l threonine. Thus the strains NZ10 rhtA23 scr/pAL4 was obtained. This strain and the parent strain were each cultivated at 37° C. for 18 hours in a nutrient broth, and 0.3 ml of the obtained culture was inoculate into 3 ml of a fermentation medium in a 20×200 mm test tube, and cultivated at 37° C. for 48 hours with a rotary shaker. The fermentation medium had the same composition as that described in Example 3, except for 0.2 g/l threonine was added instead of isoleucine.

After the cultivation, an accumulated amount of homoserine in the medium and an absorbance at 560 nm of the medium were determined by known methods. The results are presented in Table 3.

TABLE 3

| | Glucose | | | Sucrose | | |
|---|---|---|---|---|---|---|
| Strain | OD$_{560}$ | Homoserine (g/l) | Yield (%) | OD$_{560}$ | Homoserine (g/l) | Yield (%) |
| NZ10rhtA23/pAL4 | 19.3 | 7.8 | 9.7 | — | — | — |
| NZ10rhtA23 Scr/pAL4 | 20.0 | 8.0 | 10.0 | 21.4 | 12.2 | 15.2 |

As shown in Table 3, the NZ10 rhtA23 scr/pAL4 strain and its parent NZ10 rhtA23/pAL4 grew about equally and accumulated about the same amount of homoserine when cultured in glucose-containing medium. However, the NZ10 rhtA23 scr/pAL4 strain accumulated more homoserine with a higher yield when cultured in sucrose-containing medium.

EXAMPLE 5

Preparation of the E. coli Isoleucine Producing Strain Capable to Utilize Sucrose, and Isoleucine Production Using This Strain As the isoleucine-producing bacterium belonging to the genus Escherichia E. coli K-12 strain 44-3-15 was used. This strain was constructed as follows. The wild type E. coli K-12 strain VKPM B-7 was used as a parent. After the sequential procedures of NTG mutagenesis and selection for resistance to valine, 4-aza-DL-leucine and 3-hydroxy-DL-leucine, the strain 44 was obtained which contains at least two mutations in ilvGMEDA operon: a mutation in the ilvG gene (ilvG*) restoring acetohydroxy acid synthase II activity, and a mutation in ilvA gene (ilvA*) conferring threonine deaminase insensitivity to feedback inhibition by isoleucine. This strain can produce some amount of isoleucine.

On the other hand, the plasmid pVR72, a derivative of the pVR4 plasmid (Gavrilova et al., 1988, Biotechnologiya (in Russian), 4: 600–608) harboring ilvG$_5$MEDA$_{7434}$YC genes, was constructed by the introduction of the BamHI linkers into DraIII and XmaIII sites. Next, the BamHI fragment of pVR72 containing ilvG$_5$MEDA$_{7434}$YC genes with deleted promoter and attenuator was cloned into pM2, a mini-Mud vector pMu4041 derivative containing the P$_R$ promoter of the phage lambda. The resulted plasmid was used for the introduction of mini-Mu-P$_R$-ilvG*MEDPA*YC construct into the chromosome of the 44(pMH10) strain as described above. After Mu transposase induction procedure the clones were tested for their ability to produce isoleucine. Among them the most productive strain 44-3 was selected. Finally, the mini-Mu-P$_R$-thrA*BC-cat construct was transduced into the 44-3 strain from C600 Thr$^+$, Cm$^R$ as described above. Thus the strain 44-3-15 was obtained.

The isoleucine-producing strain 44-3-15 was infected with phage P1$_{vir}$ grown on the donor strains VD1 or W3350csc. The transductants were selected on M9 minimal medium containing 0.2% sucrose as a sole carbon source. Thus the strains 44-3-15 Scr and 44-3-15 Csc were obtained.

These strains and the parent strain were each cultivated at 37° C. for 18 hours in a nutrient broth, and 0.3 ml of the obtained culture was inoculated into 3 ml of a fermentation medium in a 20×200 mm test tube, and cultivated at 37° C. for 72 hours with a rotary shaker. The fermentation medium had the same composition as that described in shown in Example 3, except for isoleucine was not added. After the cultivation, an accumulated amount of isoleucine in the medium and an absorbance at 560 nm of the medium were determined by known methods. The results are presented in Table 4.

TABLE 4

| | Glucose | | | Sucrose | | |
|---|---|---|---|---|---|---|
| Strain | OD$_{560}$ | Isoleucine (g/l) | Yield (%) | OD$_{560}$ | Isoleucine (g/l) | Yield (%) |
| 44-3-15 | 16.1 | 10.4 | 13.0 | — | — | — |
| 44-3-15 Scr | 16.4 | 10.8 | 13.5 | 16.1 | 13.1 | 16.4 |
| 44-3-15 Csc | 15.3 | 10.5 | 13.1 | 16.0 | 13.6 | 17.0 |

As shown in Table 4, both sucrose utilizing strains, 44-3-15 Scr and 44-3-15 Csc, had the same growth characteristics and accumulated about the same amount of isoleucine as their parent 44-3-15 when cultured in glucose-containing medium. However, these strains accumulated more isoleucine with a higher yield when cultured in sucrose-containing medium. Besides, the 44-3-15 Csc strain (having sucrose non-PTS genes) was slightly more productive under this condition than the 44-3-15 Scr strain (having sucrose PTS genes)

EXAMPLE 6

Preparation of the E. coli Lysine Producing Strain Capable to Utilize Sucrose, and Lysine Production Using This Strain As a recipient strain producing lysine E. coli strain VL612 was used. This strain was obtained from the known E. coli strain Gif102 (Theze, J. and Saint Girons., J. Bacteriol., 118, 990–998, 1974) in the two steps. At the first step the mutants of the strain resistant to 2 mg/ml S-(2-aminoethyl)-L-cysteine were selected and among them the strain VL611 capable of producing lysine was found. At the second step, the mutation rhtA23 was introduced into VL611 as above giving the strain VL612.

The strain VL612 was infected with phage Pl$_{vir}$ grown on the donor strain VL478. The transductants were selected on M9 minimal medium containing 50 mg/l homoserine and 0.2% sucrose as a sole carbon source. Thus the strains VL613 (VKPM B-3423) was obtained. This strain and the parent strain were each cultivated at 37° C. for 18 hours in a nutrient broth, and 0.3 ml of the obtained culture was inoculate into 3 ml of a fermentation medium in a 20×200 mm test tube, and cultivated at 37° C. for 72 hours with a rotary shaker. The fermentation medium had the same composition as that described in shown in Example 2, except for 0.2 g/l homoserine was added. After the cultivation, an accumulated amount of lysine in the medium and an absorbance at 560 nm of the medium were determined by known methods. The results are presented in Table 5.

TABLE 5

| | Glucose | | | Sucrose | | |
|---|---|---|---|---|---|---|
| Strain | OD$_{560}$ | Lysine (g/l) | Yield (%) | OD$_{560}$ | Lysine (g/l) | Yield (%) |
| VL612 | 11.5 | 2.8 | 5.6 | — | — | — |
| VL613 | 11.2 | 2.7 | 5.4 | 11.4 | 4.2 | 8.4 |

As shown in Table 5, the VL612 strain and the VL613 strain grew about equally in glucose-containing medium and accumulated about the same amount of lysine. However, the VL613 strain accumulated more lysine with a higher yield when cultured in sucrose-containing medium.

EXAMPLE 7

Preparation of the E. coli Valine Producing Strain Capable to Utilize Sucrose, and Valine Production Using This Strain As valine producing bacterium belonging to the genus Escherichia E. coli strain VL1971 was used. This strain is a derivative of the known strain VL1970 (VKPM B-4411, U.S. Pat. No. 5,658,766) to which the rhtA23 mutation was introduced as described in Example 1.

The *E. coli* strain VL1971 was infected with the phage P1$_{vir}$ grown on the VL478 donor strain and plated to the M9 minimal medium containing 0.2% sucrose as a sole carbon source. The transductants grown after 40 h were picked, purified and among them the valine producing strain, VL1972 (VKPM B-4413), capable to utilize sucrose was selected.

VL1971 and VL1972 were each cultivated at 37° C. for 18 hours in a nutrient broth, and 0.3 ml of the obtained culture was inoculated into 3 ml of a fermentation medium in a 20×200 mm test tube, and cultivated at 37° C. for 72 hours with a rotary shaker. The fermentation medium had the same composition as that described in shown in Example 3. After the cultivation, an accumulated amount of valine in the medium and an absorbance at 560 nm of the medium were determined by known methods. The results are shown in Table 6.

TABLE 6

| | Glucose | | | Sucrose | | |
|---|---|---|---|---|---|---|
| Strain | OD$_{560}$ | Valine (g/l) | Yield (%) | OD$_{560}$ | Valine (g/l) | Yield (%) |
| VL1971 | 12.4 | 8.0 | 10.0 | — | — | — |
| VL1972 | 12.6 | 8.2 | 10.2 | 14.4 | 11.2 | 14.0 |

As shown in Table 6, the VL1971 and VL1972 strains grew equally and accumulated about the same amount of valine when cultured in glucose-containing medium. However, the VL1972 strain accumulated more valine with a higher yield when cultured in sucrose-containing medium.

It is worthy to note that PTS sucrose genes confer the higher productivity to valine producer although phosphoenol pyruvate is not necessary to valine synthesis.

EXAMPLE 8

Preparation of the *E. coli* Tryptophan Producing Strain Capable to Utilize Sucrose, and Tryptophan Production Using This Strain As a recipient strain of bacterium belonging to the genus *Escherichia*, the strain SV164(pGH5) (WO94/08031) was used.

The tryptophan overproducing strain SV164(pGH5) was infected with phage P1$_{vir}$ grown on the donor strains VD1 or W3350csc. The transductants were selected on M9 minimal medium containing 50 mg/l tyrosine, 50 mg/ml phenylalanine, 0.2% sucrose as a sole carbon source and 15 mg/l tetracycline. Thus the strains SV164scr (pGH5) and SV164csc (pGH5), respectively, were obtained.

These strains and the parent strain were each cultivated at 29° C. for 18 hours in a nutrient broth, and 0.3 ml of the obtained culture was inoculated into 3 ml of a fermentation medium having the following composition in a 20×200 mm test tube, and cultivated at 29° C. for 40 hours with a rotary shaker.

| Fermentation medium composition (g/l): | |
|---|---|
| Glucose (or Sucrose) | 40 |
| phenylalanine | 0.1 |

-continued

| Fermentation medium composition (g/l): | |
|---|---|
| tyrosine | 0.1 |
| (NH$_4$)$_2$SO$_4$ | 15 |
| KH$_2$PO$_4$ | 1.5 |
| NaCl | 0.5 |
| MgSO$_4$ × 7H$_2$O | 0.3 |
| CaCl$_2$ × 2H$_2$O | 0.015 |
| FeSO$_4$ × 7H$_2$O | 0.075 |
| Na$_3$-citrate | 1 |
| Na$_2$MoO$_4$ × 2H$_2$O | 0.00015 |
| H$_3$BO$_3$ | 0.0025 |
| CoCl$_2$ × 6H$_2$O | 0.0007 |
| CuSO$_4$ × 5H$_2$O | 0.00025 |
| MnCl$_2$ × 4H$_2$O | 0.0016 |
| ZnSO$_4$ × 7H$_2$O | 0.0003 |
| Thiamine HCl | 0.005 |
| Pyridoxine | 0.03 |
| Corn Steep Solids (AJINOMOTO) | 2 |
| CaCO$_3$ | 30 |
| Tetracycline | 0.015 |

After the cultivation, an accumulated amount of tryptophan and an absorbance at 560 nm of the medium were determined by known methods. The results are presented in Table 7. As shown in Table 7, both sucrose utilizing strains, SV164scr(pGH5) and SV164csc(pGH5), had nearly the same growth characteristics and accumulated about the same amount of tryptophan as their parent SV164(pGH5) when cultivated in glucose-containing medium. However, these strains accumulated more tryptophan with a higher yield when cultivated in sucrose-containing medium. Moreover, the SV164csc(pGH5) strain (having sucrose non-PTS genes) was more productive under this conditions than the strain SV164scr(pGH5) (having sucrose PTS genes).

TABLE 7

| | Glucose | | | Sucrose | | |
|---|---|---|---|---|---|---|
| Strain | OD$_{560}$ | Tryptophan (g/l) | Yield (%) | OD$_{560}$ | Tryptophan (g/l) | Yield (%) |
| SV164 (pGH5) | 6.0 | 5.0 | 12.5 | — | — | — |
| SV164 scr (pGH5) | 6.2 | 5.1 | 12.7 | 6.2 | 5.5 | 13.7 |
| SV164 csc (pGH5) | 6.0 | 5.0 | 12.5 | 6.2 | 5.6 | 14.0 |

What is claimed is:

1. A method for producing an amino acid comprising
   a) cultivating in a culture medium an isolated *Escherichia coli* bacterium which has been constructed from a sucrose non-assimilative *Escherichia coli* strain, wherein the bacterium harbors csc genes originating from *Escherichia coil* selected from the group consisting of strain EC3132 and strain W3350csc, and comprising genes coding for a permease, invertase and fructokinase, and said bacterium having an ability to cause accumulation of an amino acid in a medium when the bacterium is cultured in the medium in an amount higher than is produced from a bacterium not harboring said csc genes, and
   b) collecting said amino acid from said medium.

2. The method according to claim 1, wherein said amino acid is selected from the group consisting of threonine, homoserine, isoleucine, lysine, valine, and tryptophan.

* * * * *

UNITED STATES PATENT AND TRADEMARK OFFICE
CERTIFICATE OF CORRECTION

PATENT NO. : 6,960,455 B2
DATED : November 1, 2005
INVENTOR(S) : Livshits et al.

It is certified that error appears in the above-identified patent and that said Letters Patent is hereby corrected as shown below:

<u>Title page,</u>
Item [75], Inventors, should read:
-- Vitaliy Arkadyevich Livshits, Moscow (RU); Vera Georgievna Doroshenko, Moscow (RU); Sergei Vladimirovich Mashko, Moscow (RU); Valery Zavenovich Akhverdian, Moscow (RU); Yury Ivanovich Kozlov, Moscow (RU) --.

Signed and Sealed this

Sixteenth Day of May, 2006

JON W. DUDAS
*Director of the United States Patent and Trademark Office*